United States Patent
Ghosh

(10) Patent No.: US 11,366,121 B2
(45) Date of Patent: Jun. 21, 2022

(54) SPECIFIC GNAI:GIV INTERACTION SCREENING ASSAYS, METHODS AND COMPOSITIONS

(71) Applicant: The Regents of the University of California, Oakland, CA (US)

(72) Inventor: Pradipta Ghosh, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 106 days.

(21) Appl. No.: 16/487,462

(22) PCT Filed: Feb. 22, 2018

(86) PCT No.: PCT/US2018/019127
§ 371 (c)(1),
(2) Date: Aug. 21, 2019

(87) PCT Pub. No.: WO2018/156697
PCT Pub. Date: Aug. 30, 2018

(65) Prior Publication Data
US 2020/0064352 A1    Feb. 27, 2020

Related U.S. Application Data

(60) Provisional application No. 62/461,925, filed on Feb. 22, 2017, provisional application No. 62/502,029, filed on May 5, 2017.

(51) Int. Cl.
*G01N 33/68* (2006.01)
*A61K 31/185* (2006.01)
*C07K 7/08* (2006.01)
*C07K 14/47* (2006.01)
*C07K 14/72* (2006.01)

(52) U.S. Cl.
CPC ....... *G01N 33/6845* (2013.01); *A61K 31/185* (2013.01); *C07K 7/08* (2013.01); *C07K 14/47* (2013.01); *C07K 14/723* (2013.01); *G01N 2333/726* (2013.01); *G01N 2500/02* (2013.01)

(58) Field of Classification Search
CPC .......... C12N 2310/14; C12N 2310/531; C12N 15/113; G01N 2333/726; G01N 2500/02; G01N 33/6845
See application file for complete search history.

(56) References Cited

U.S. PATENT DOCUMENTS 6,277,874 B1 *  8/2001  Crutcher .............. A61K 31/185
                                                514/367
2016/0362464 A1  12/2016  Ghosh
2018/0104307 A1   4/2018  Ghosh

FOREIGN PATENT DOCUMENTS

WO    2016/168702 A1    10/2016

OTHER PUBLICATIONS

Roos et al. (Oncotarget 2017 8:12234), (Year: 2017).*
Cossu et al. (Proteins 2015 83:612). (Year: 2015).*
Mackay Genetics 2003, vol. 163, p. 1365-1373 (Year: 2003).*
Kuno J Biol. Chern 1993, vol. 268, p. 13510-13518 (Year: 1993).*
Ashmun Blood 1992, vol. 79, p. 3344-3349 (Year: 1992).*
Bowie et al. Science, 1990 vol. 247:1306-1310 (Year: 1990).*
PCT International Search Report and Written Opinion for PCT Application No. PCT/US2018/019127 dated May 17, 2018 (8 pages).
Blazer et al., "A Nanomolar Potency Small Molecule Inhibitor of Regulator of G Protein Signaling (RGS) Proteins," Biochemistry, 2011, 50(15):3181-3192.
Digiacomo et al., "The Gαi-GIV Binding Interace is a Druggable Protein-Protein Interaction," Scientific Reports, 2017, 7:8575 (17 pages).
Fitzgerald et al., "Chemical Genetics Reveals an RGS/G-Protein Role in the Action of a Compound," PLoS Genetics, 2006, 2(4):e57:0425-0437.

* cited by examiner

*Primary Examiner* — Changhwa J Cheu
(74) *Attorney, Agent, or Firm* — Eversheds Sutherland (US) LLP

(57) ABSTRACT

Research tool assay for identifying a specific modulator of GNAI, compositions and methods of use. The assay includes combining a drug candidate with GNAI and a C-terminal GIV peptide and determining if the drug candidate inhibits GNAI interaction with the C-terminal GIV peptide; and combining the drug candidate with GNAI and a DAPLE peptide and determining if the drug candidate inhibits GNAI interaction with DAPLE peptide. Also provided are compositions and methods of treatment relating to the same.

2 Claims, 24 Drawing Sheets

Specification includes a Sequence Listing.

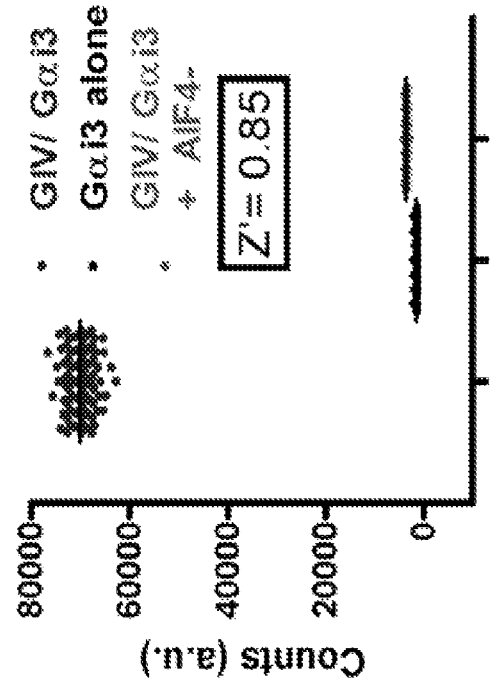
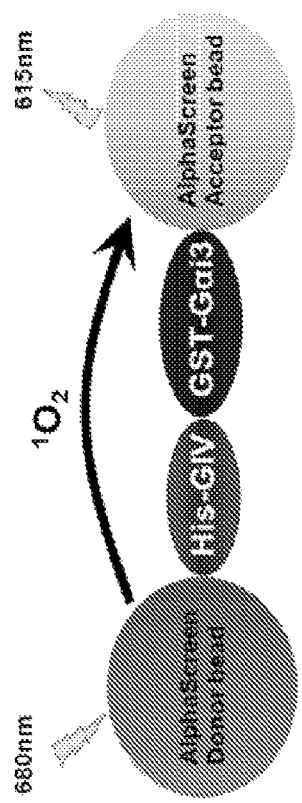
FIG. 9A

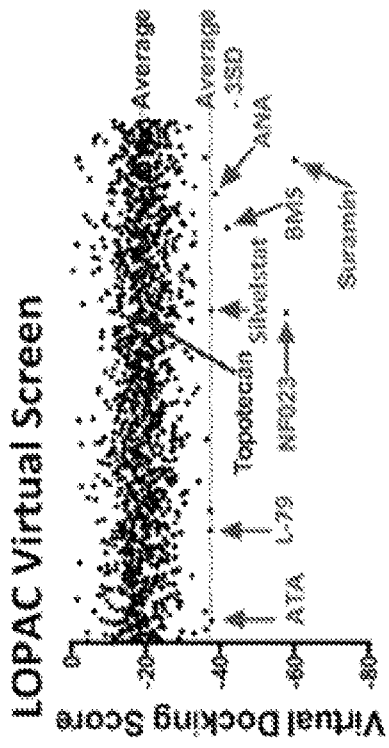
FIG. 11A
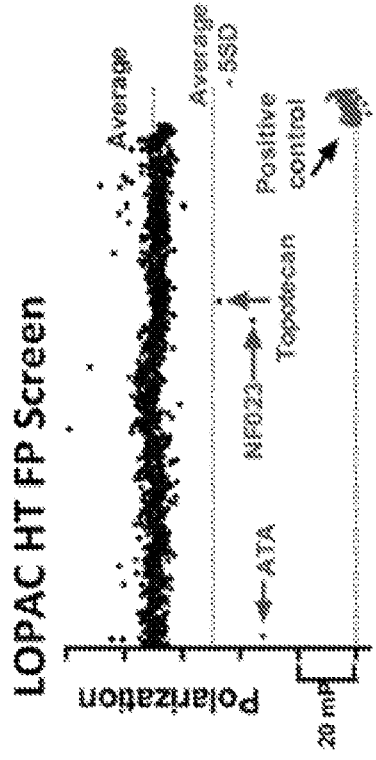
FIG. 11C
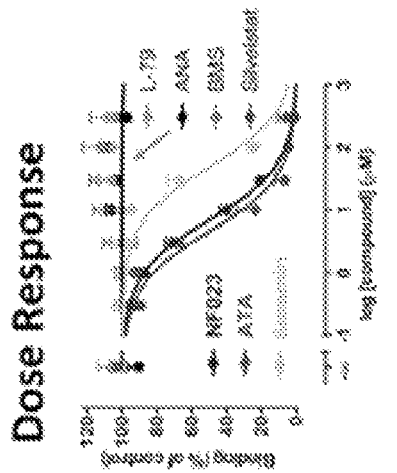
FIG. 11B
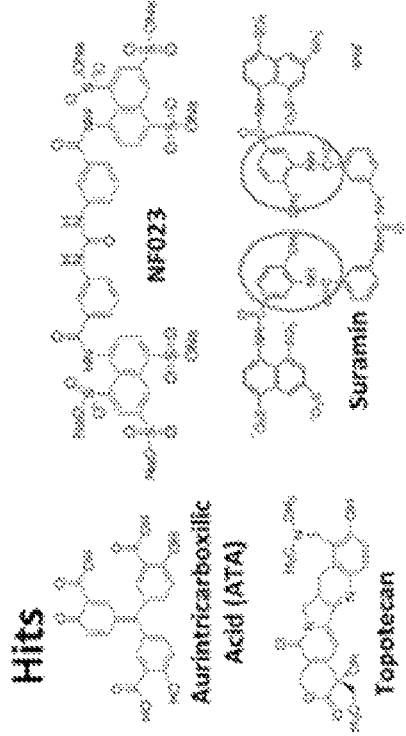
FIG. 11D
FIG. 11E

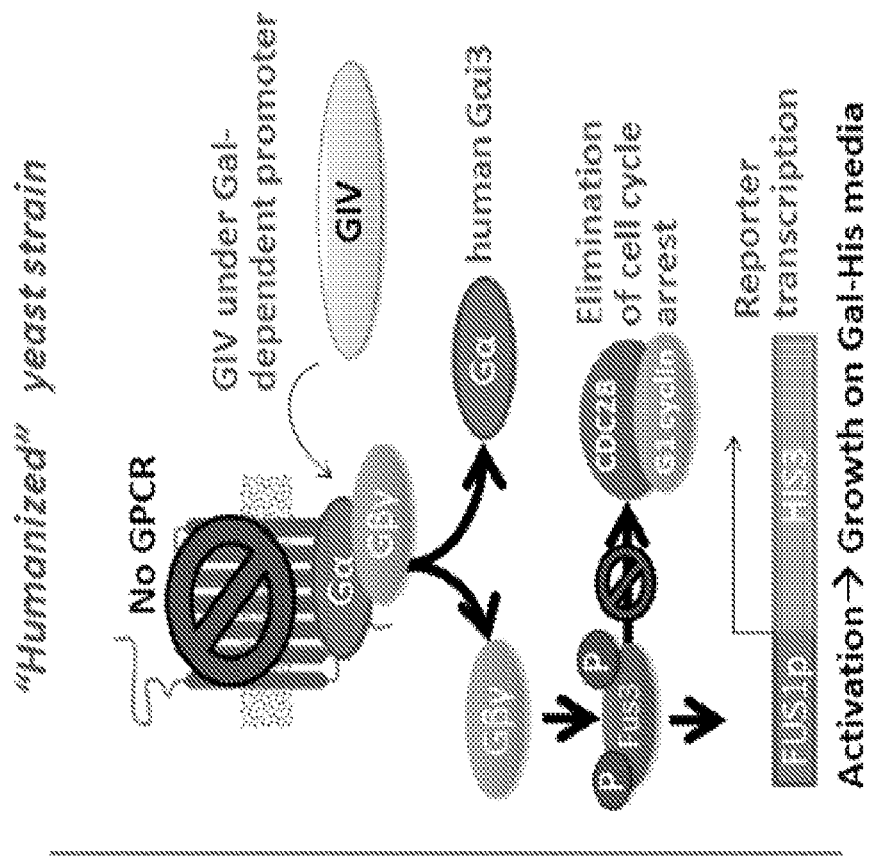
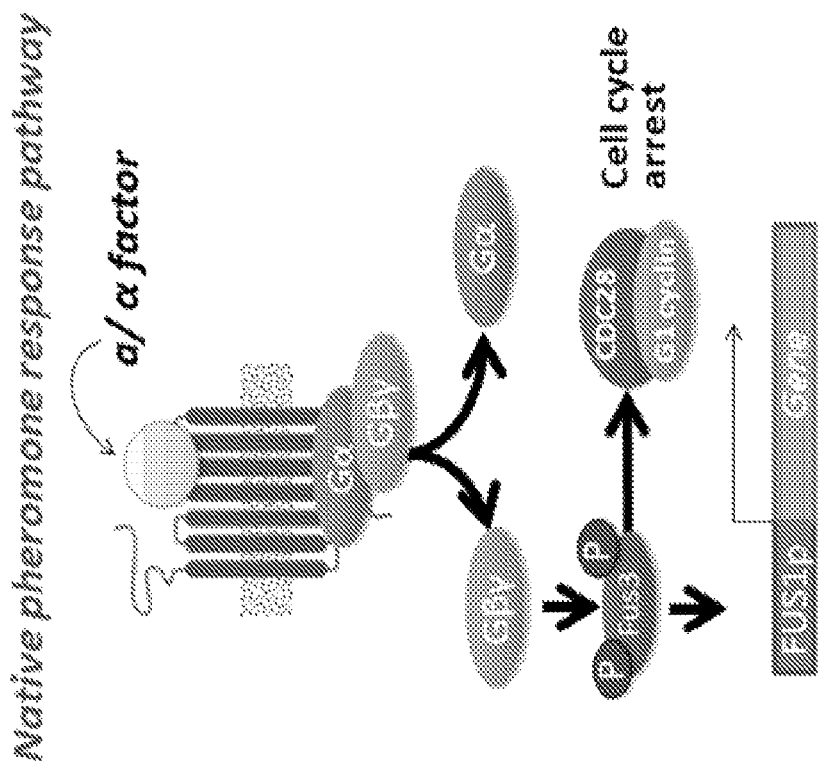
FIG. 13B

GIV GBA peptide: KTGSPGSEVVTLQQFLEESNKLTSVQIKSSS (SEQ ID NO.1)
DAPLE GBA peptide: SASPSSEMVTLEEFLEESNRSSPTHDTPSCRDDL (SEQ ID NO.2)

|  |  | GIV | | | DAPLE | | | RGS12 | | |
|---|---|---|---|---|---|---|---|---|---|---|
|  |  | Kd ± SEM | | Fold change | Kd ± SEM | | Fold change | Kd ± SEM | | Fold change |
|  | WT | 0.561 | ± 0.034 | 1.000 | 0.303 | ± 0.017 | 1.000 | 0.064 | ± 0.004 | 1.000 |
|  | K35A | >10 | | >20 | 6.954 | ± 1.138 | 22.952 | 0.152 | ± 0.010 | 2.000 |
| β1/P-loop | L36A | 0.706 | ± 0.062 | 1.215 | 0.559 | ± 0.029 | 1.844 | 0.119 | ± 0.009 | 2.193 |
|  | L37A | 5.479 | ± 0.854 | 9.622 | 0.411 | ± 0.046 | 1.357 | 0.088 | ± 0.008 | 1.464 |
|  | L39A | 3.079 | ± 0.319 | 5.798 | 1.639 | ± 0.289 | 5.079 | 0.176 | ± 0.021 | 3.232 |
| Switch1 | G42R | 0.377 | ± 0.036 | 0.649 | 0.246 | ± 0.027 | 0.842 | 0.094 | ± 0.006 | 1.659 |
|  | I184A | 1.907 | ± 0.206 | 3.261 | 0.919 | ± 0.126 | 3.053 | 0.083 | ± 0.007 | 1.532 |
|  | N211A | >20 | | >20 | >20 | | >20 | 0.061 | ± 0.005 | 1.115 |
| Switch II | F215A | >10 | | >10 | 6.836 | ± 1.714 | 23.162 | 0.561 | ± 0.035 | 10.127 |
|  | V218A | 0.362 | ± 0.033 | 0.623 | 0.217 | ± 0.025 | 0.715 | 0.104 | ± 0.008 | 1.917 |
| α3 helix | L249V | 1.367 | ± 0.199 | 2.352 | 0.559 | ± 0.078 | 1.846 | 0.084 | ± 0.009 | 1.537 |
|  | L249H | 1.407 | ± 0.029 | 2.420 | 2.410 | ± 0.391 | 7.952 | 0.066 | ± 0.009 | 1.224 |
|  | S252A | 0.243 | ± 0.014 | 0.417 | 0.115 | ± 0.014 | 0.378 | 0.035 | ± 0.006 | 0.644 |
|  | S252D | 3.098 | ± 0.362 | 5.337 | 4.532 | ± 0.530 | 14.927 | 0.034 | ± 0.003 | 0.628 |
| α3/β5 loop | N256A | 1.641 | ± 0.069 | 2.114 | 0.834 | ± 0.069 | 2.691 | 0.077 | ± 0.005 | 1.415 |
|  | N256E | >20 | | >20 | >20 | | >20 | 0.311 | ± 0.044 | 5.777 |
|  | K287A | 0.870 | ± 0.067 | 1.766 | 0.710 | ± 0.071 | 2.343 | 0.096 | ± 0.009 | 1.584 |
|  | W288F | 1.611 | ± 0.183 | 2.608 | 0.289 | ± 0.044 | 1.929 | 0.063 | ± 0.007 | 1.062 |
| α4/β6 loop | F259A | 1.264 | ± 0.113 | 2.558 | 0.606 | ± 0.084 | 2.948 | 0.187 | ± 0.046 | 3.429 |
|  | R313A | 0.796 | ± 0.062 | 1.522 | 0.666 | ± 0.082 | 1.991 | 0.072 | ± 0.006 | 1.221 |
|  | K317A | 0.693 | ± 0.028 | 1.204 | 0.263 | ± 0.016 | 0.867 | 0.082 | ± 0.007 | 1.501 |
|  | K317M | 0.850 | ± 0.066 | 1.098 | 0.441 | ± 0.044 | 1.434 | 0.101 | ± 0.008 | 1.842 |

FIG. 14

SPECIFIC GNAI:GIV INTERACTION SCREENING ASSAYS, METHODS AND COMPOSITIONS

CROSS REFERENCE TO RELATED APPLICATIONS

This application claims the priority benefit of PCT/US2018/019127 filed on Feb. 22, 2018 which claims priority benefit to U.S. Provisional Patent Application Ser. 62/461,925 and 62/502,029, filed Feb. 22 and May 5, 2017, respectively, the entire contents of which are incorporated by reference.

GOVERNMENT SPONSORSHIP

This invention was made with government support under grant CA160911 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 20, 2018, is named 24978-0380_SL.txt and is 1,034 bytes in size.

FIELD OF THE INVENTION

The present invention generally relates to the G-protein system and methods of identifying selective inhibitors thereof.

SUMMARY OF THE INVENTION

The inventions disclosed are high-throughput screening assays to identify small molecule specific inhibitors of G protein interactions, in particular inhibitors of the guanine nucleotide-binding protein alpha (GNAI):Girdin (GIV) peptide interface, as drug candidates, methods of use and compositions resulting therefrom. The invention provides high-throughput (HTP) screening assays for compounds which act as an inhibitor of interactions between GNAI:GIV, and do not act as an inhibitor of interactions between GNAI:Dvl-associated protein with high frequency of leucine (DAPLE).

BRIEF DESCRIPTION OF THE DRAWINGS

FIG. 9A. Secondary/counter-screen assay (1) AlphaScreen: orthogonal to primary assay.

FIGS. 11A-11E. A HTS-compatible fluorescence polarization (FP) assay to monitor the GIV:Gαi3 interaction.

FIG. 13B. Follow-up assays (2) validation of a "humanized" yeast-based system to monitor G protein activation by GIV.

FIG. 14. Kd's determined from fluorescence polarization assays with FITC peptides and hGαi3.

FIG. 20A is GIV concentration is high (5 µM), simulations predict that cAMP concentration does not vary much in response to increasing EGFR copy number. FIG. 20B is an increase in cAMP AUC over time is pronounced for GIV=0 µM (green bars) while FIG. 20C is a very small change in the AUC over time for GIV=5 µM (red bars).

DETAILED DESCRIPTION

Figure 1:
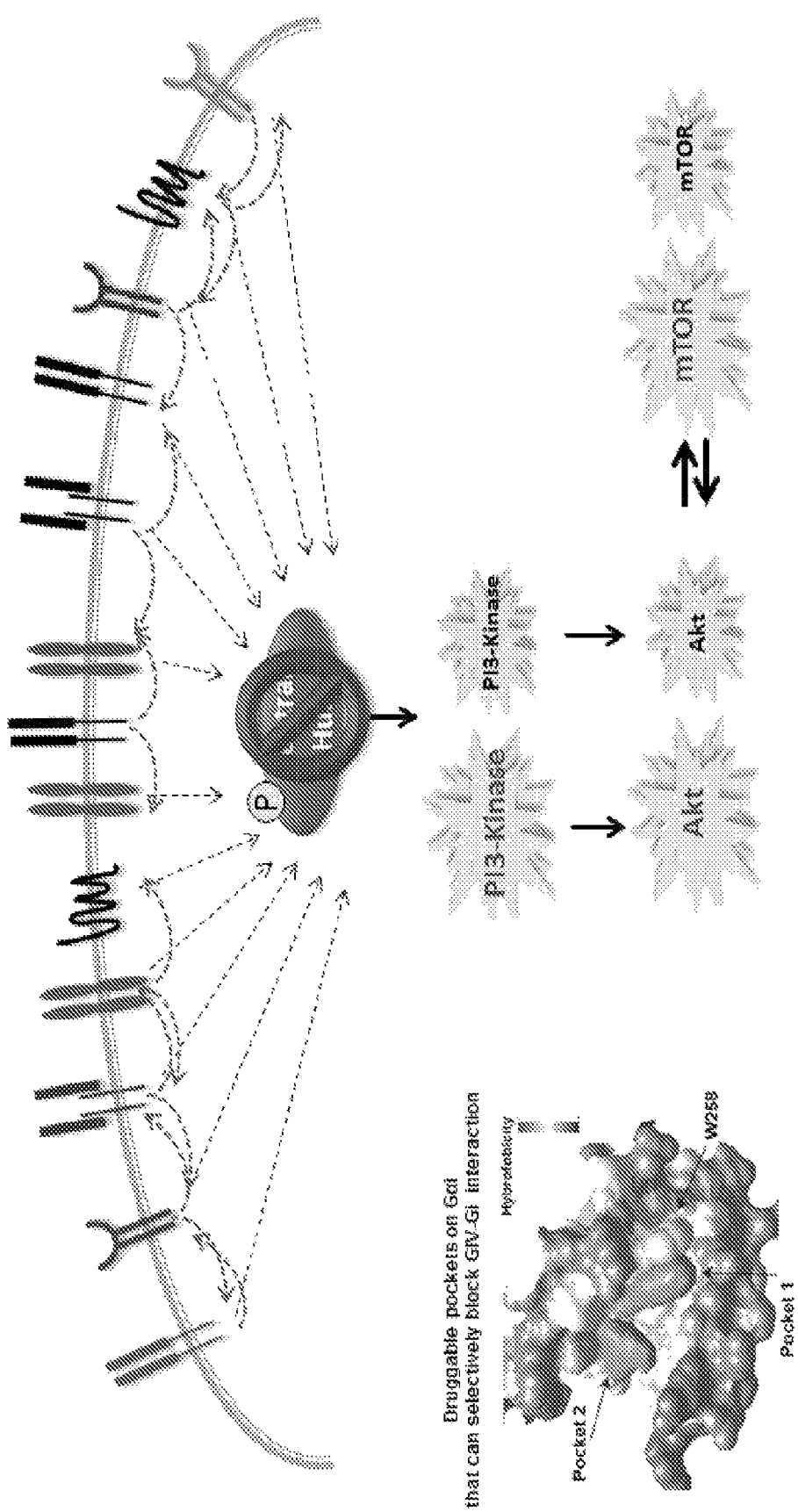
FIG. 1. GIV-GEF provides a strategy to annihilate pathologic signaling downstream of multiple receptors.
Figure 2:
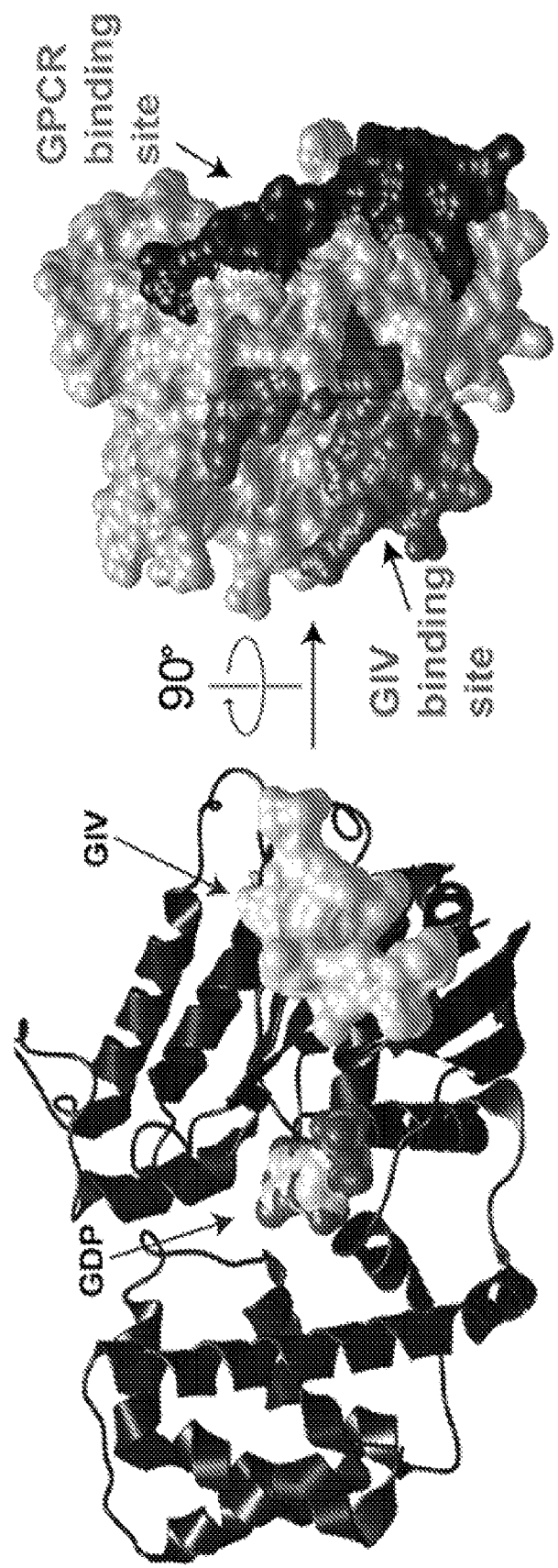
FIG. 2. GIV and GPCRs bind to G protein at different sites.
Figure 3:
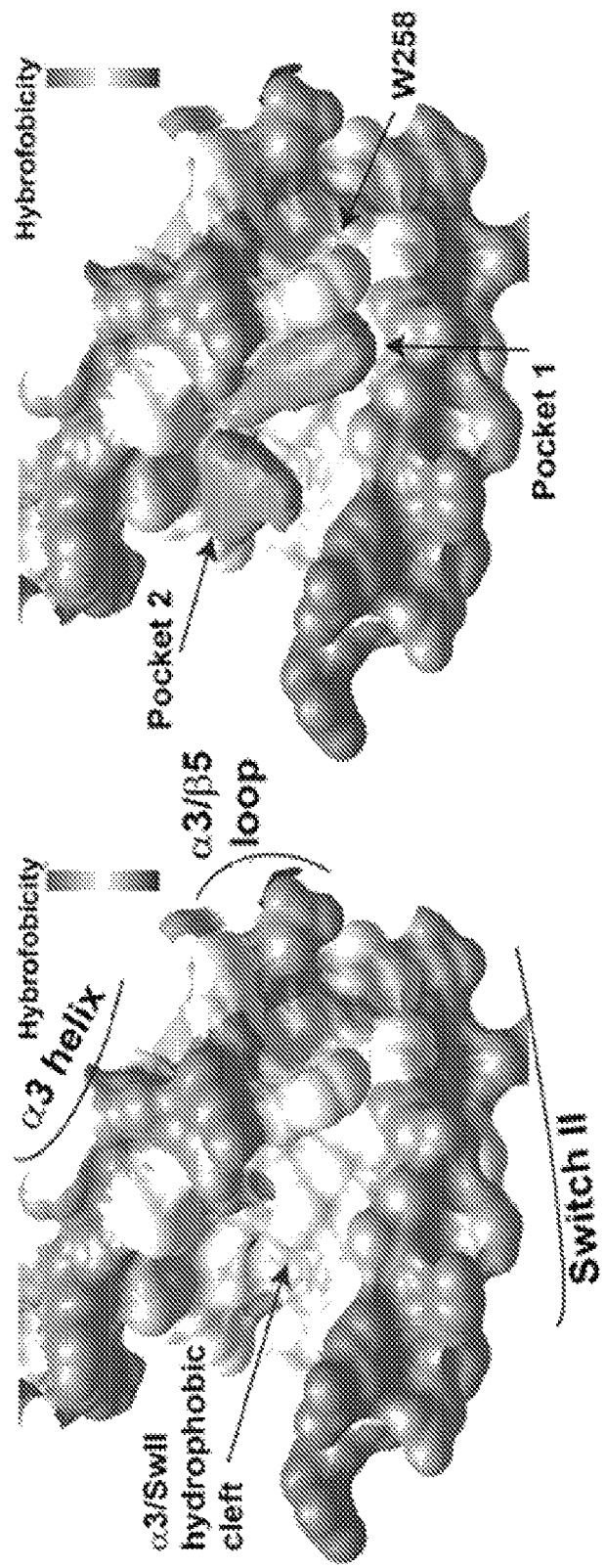
FIG. 3. GIV binding site is a hydrophobic cleft with predicted druggable pockets.
Figure 4:
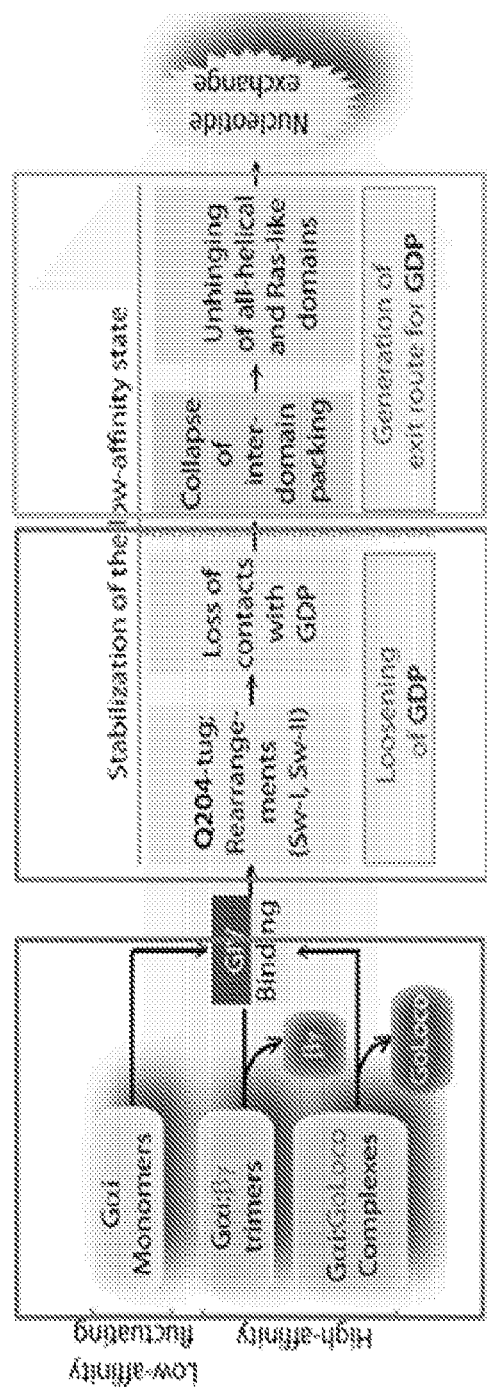
FIG. 4. Structural basis for nucleotide exchange by GIV-GEM.
Figures 5A, 5B, 5C:
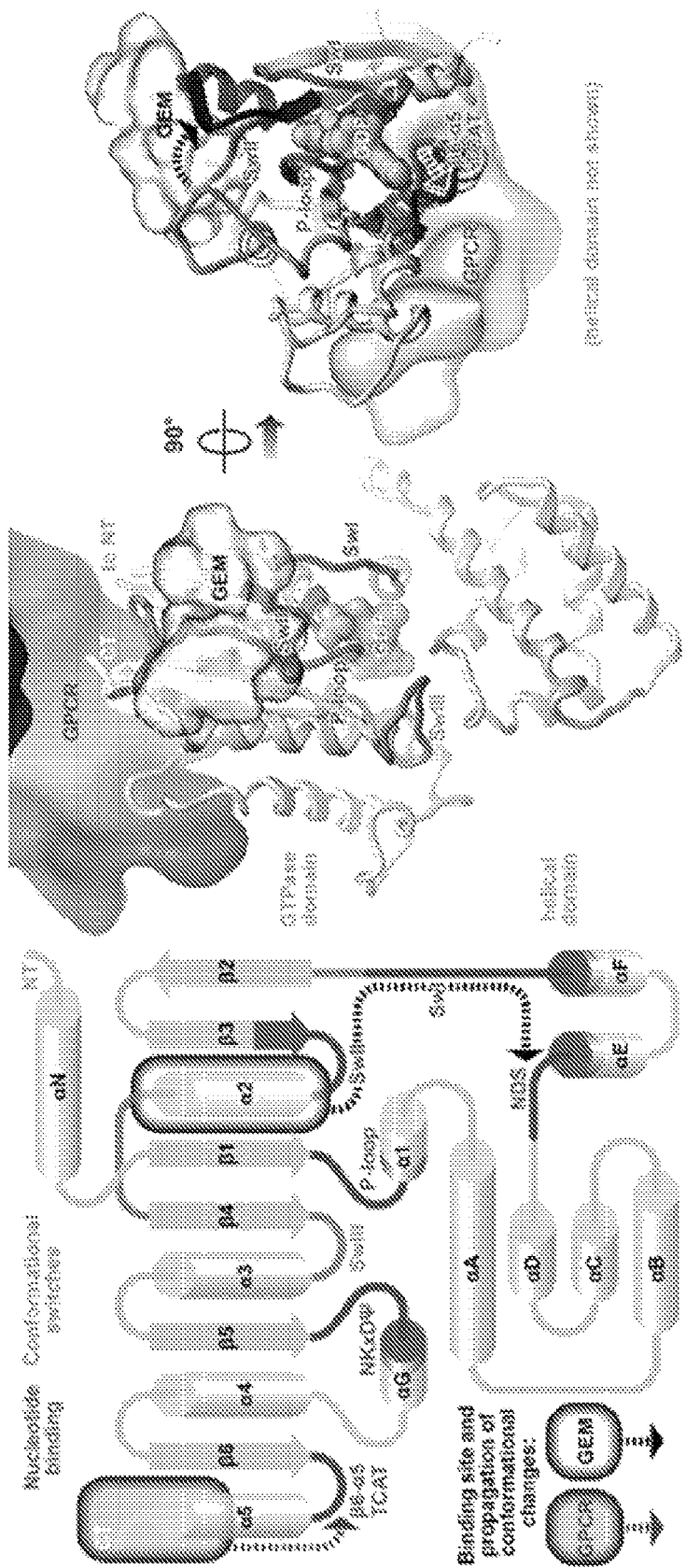
FIGS. 5A-5C. GIV-GEM binding that activates G proteins via mechanisms unlike GPCRs.
Figure 6A:
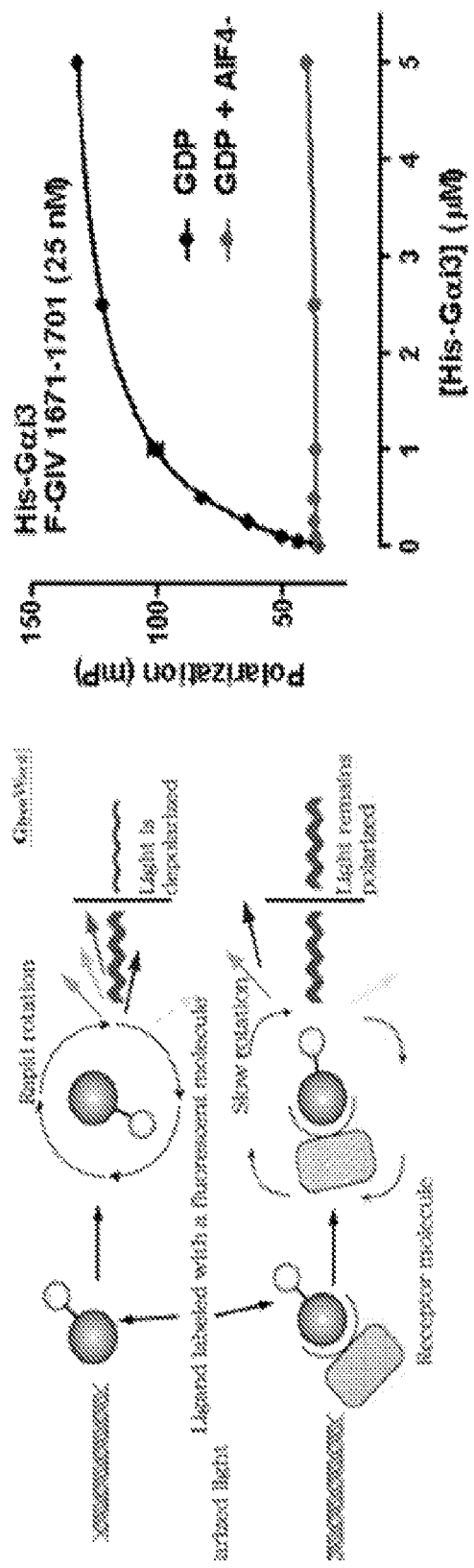
FIG. 6A. HTS-compatible assay development for the GIV-Gαi interaction providing a positive control for inhibition.
Figure 6B:
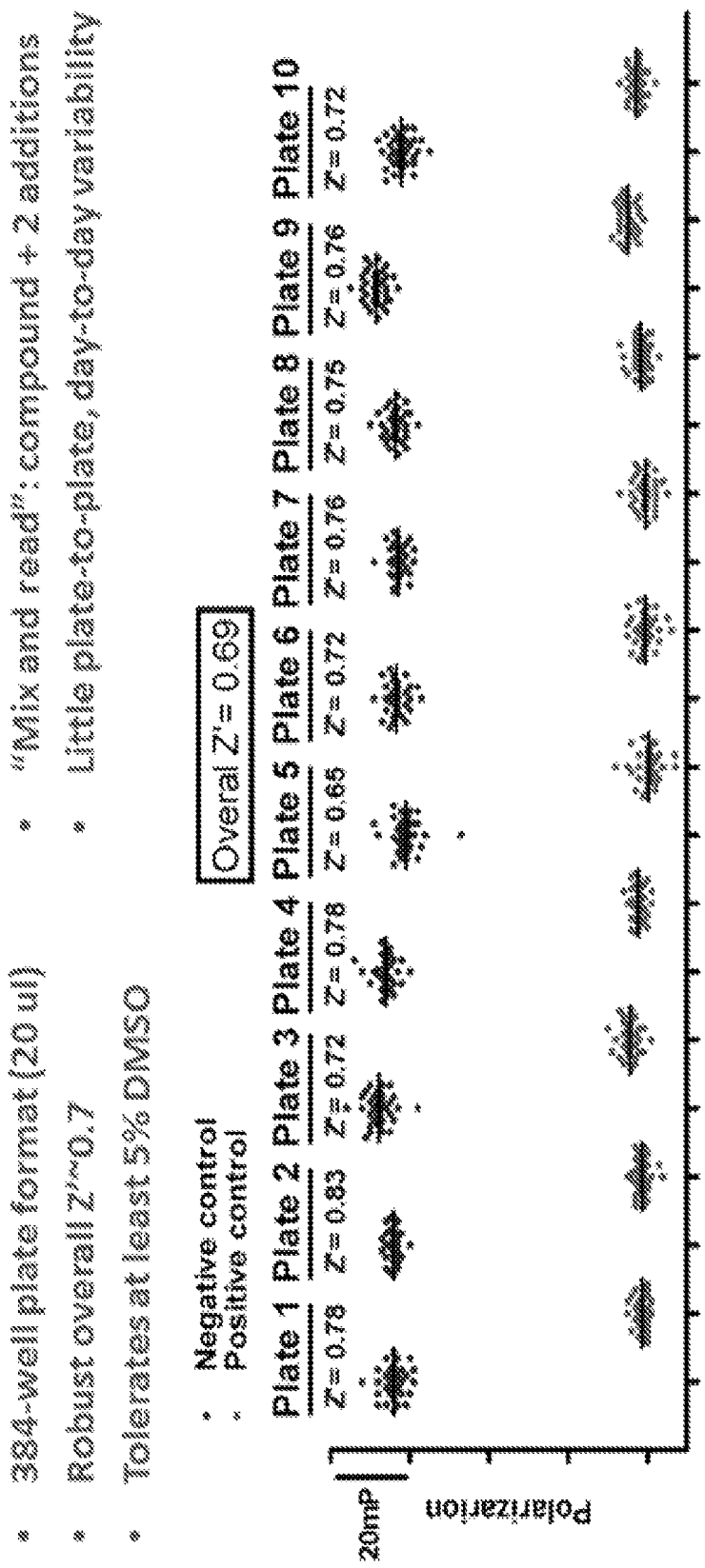
FIG. 6B. HTS-compatible assay development for the GIV-Gαi interaction showing robustness.
Figure 7:
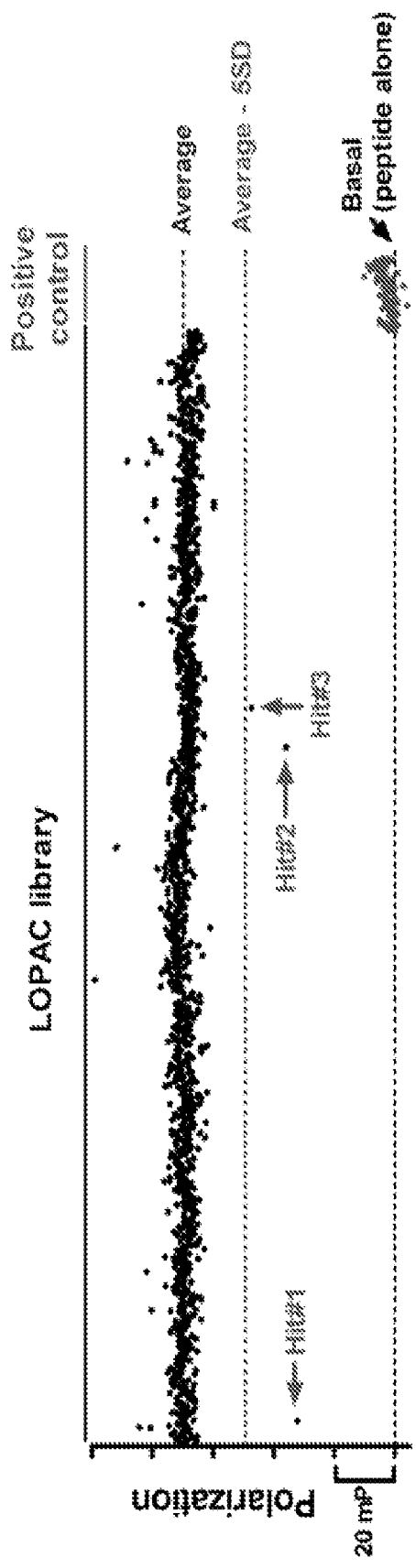
FIG. 7. GIV-Gαi inhibitor pilot screen LOPAC 1280 library (known bioactives).
Figures 8A, 8B:
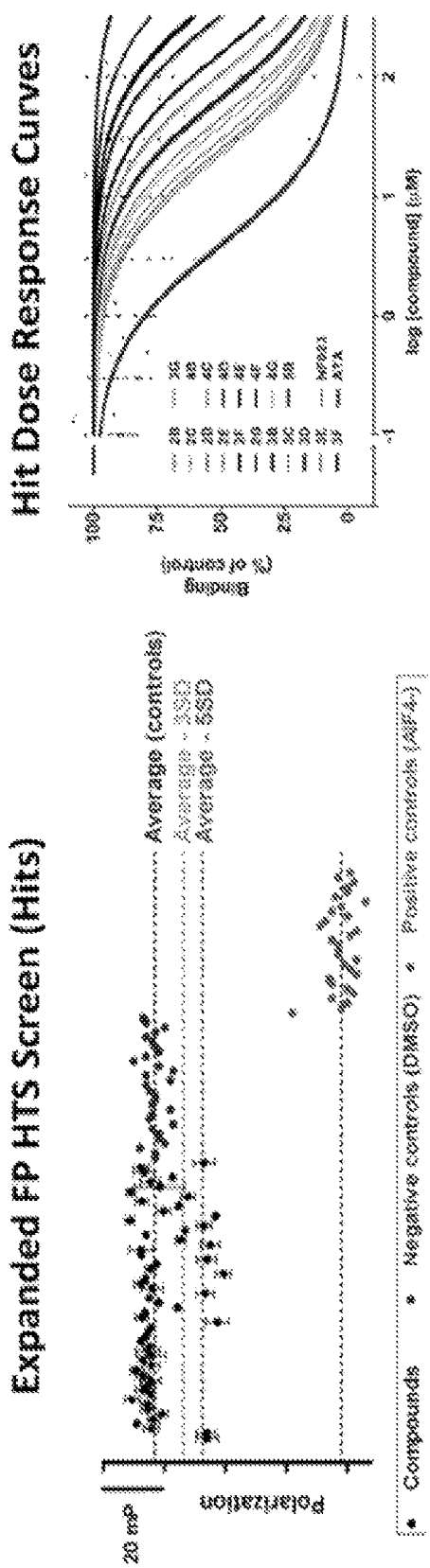
FIGS. 8A-8B. Expansion of the GIV:Gαi3 inhibitor screening to 30,000 compounds. "Re-test" plate of hits identified by the HTS-FP assay along side DMSO (negative) and ALF4-(positive).
Figure 9B:
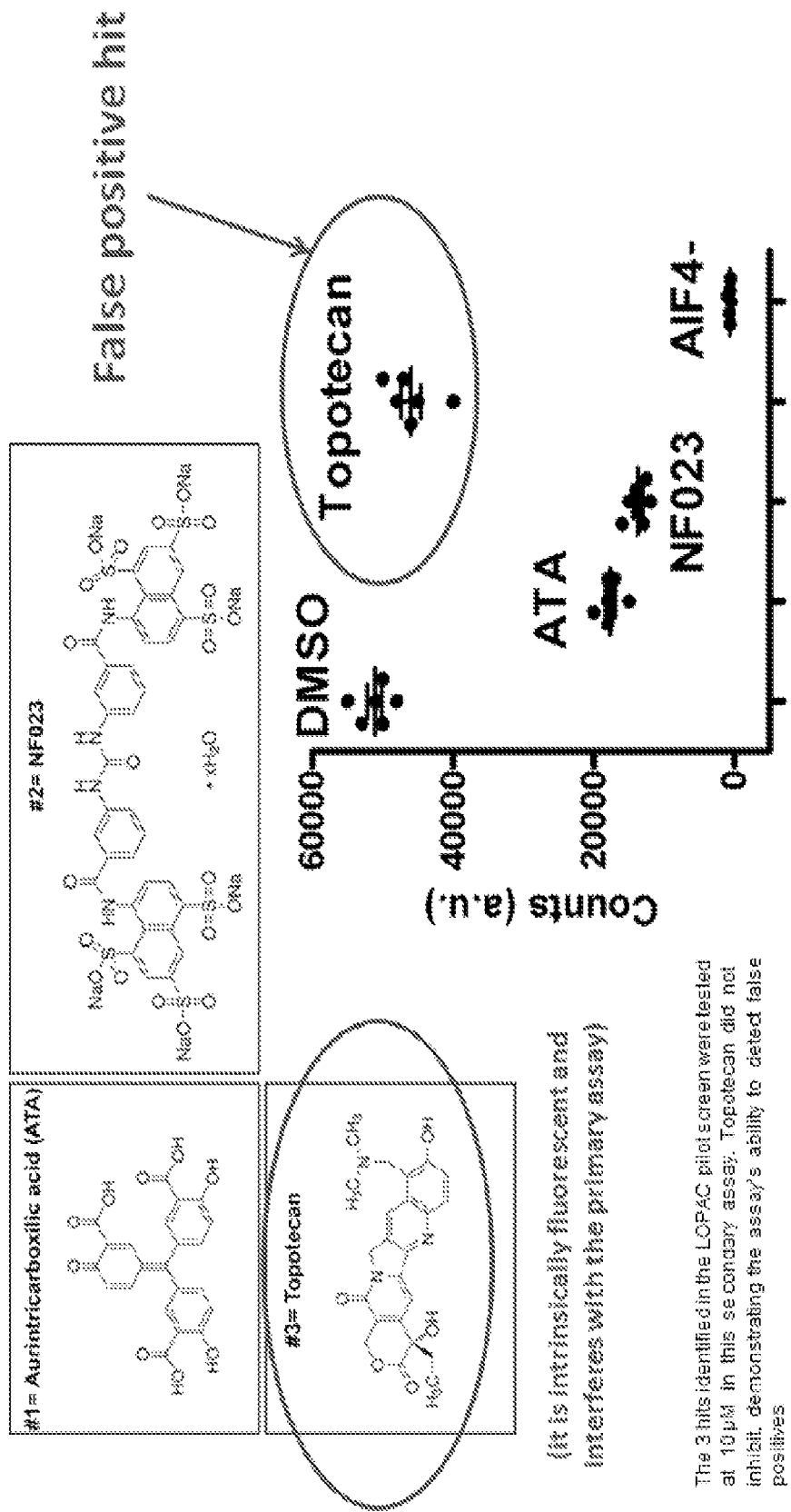
FIG. 9B. Secondary/counter-screen assay (2) validation of hits from pilot screen, suitable to filter false positives.
Figure 10:
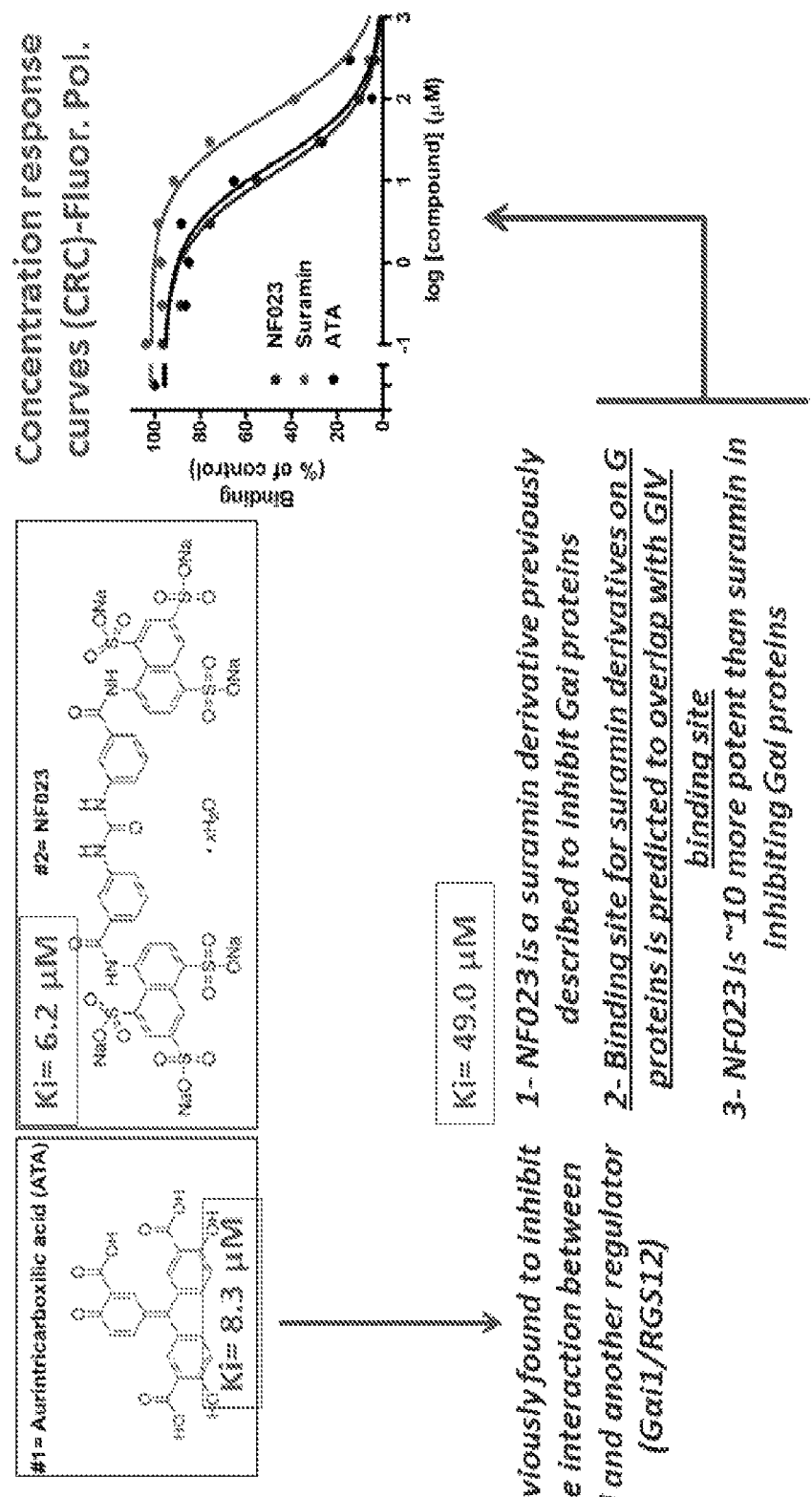
FIG. 10. Further analysis of confirmed hits validate the assay to identify inhibitors of the target.
Figure 12:
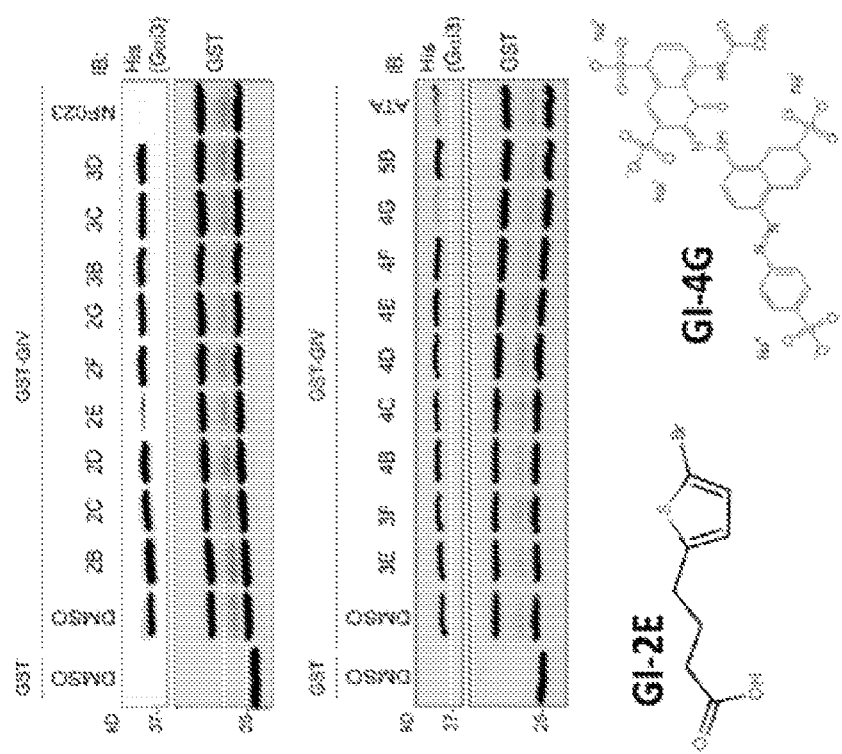
FIG. 12. GI-2E is a candidate.
Figure 13A:
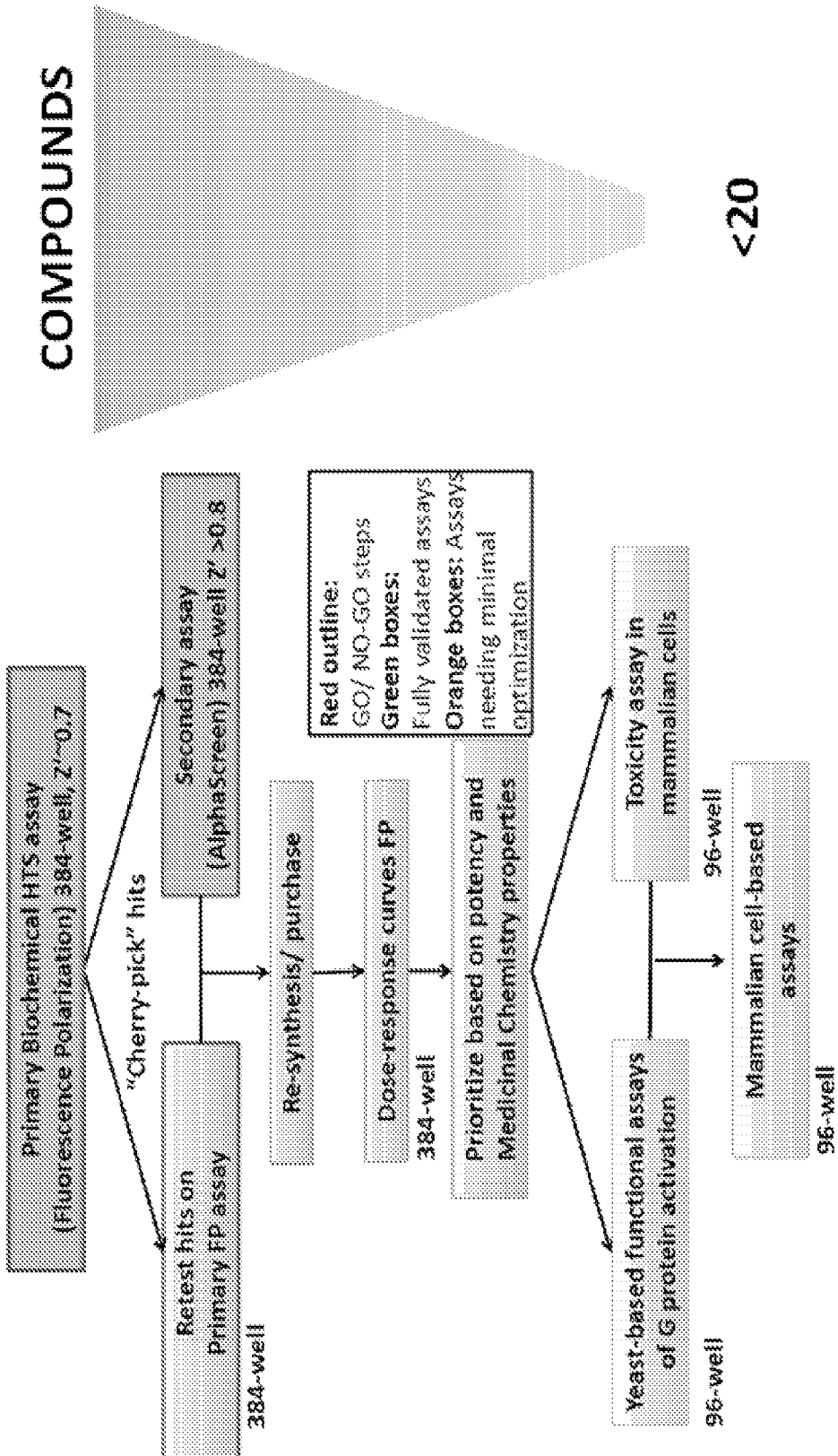
FIG. 13A. Follow-up assays (1) flowchart.
Figure 13C:
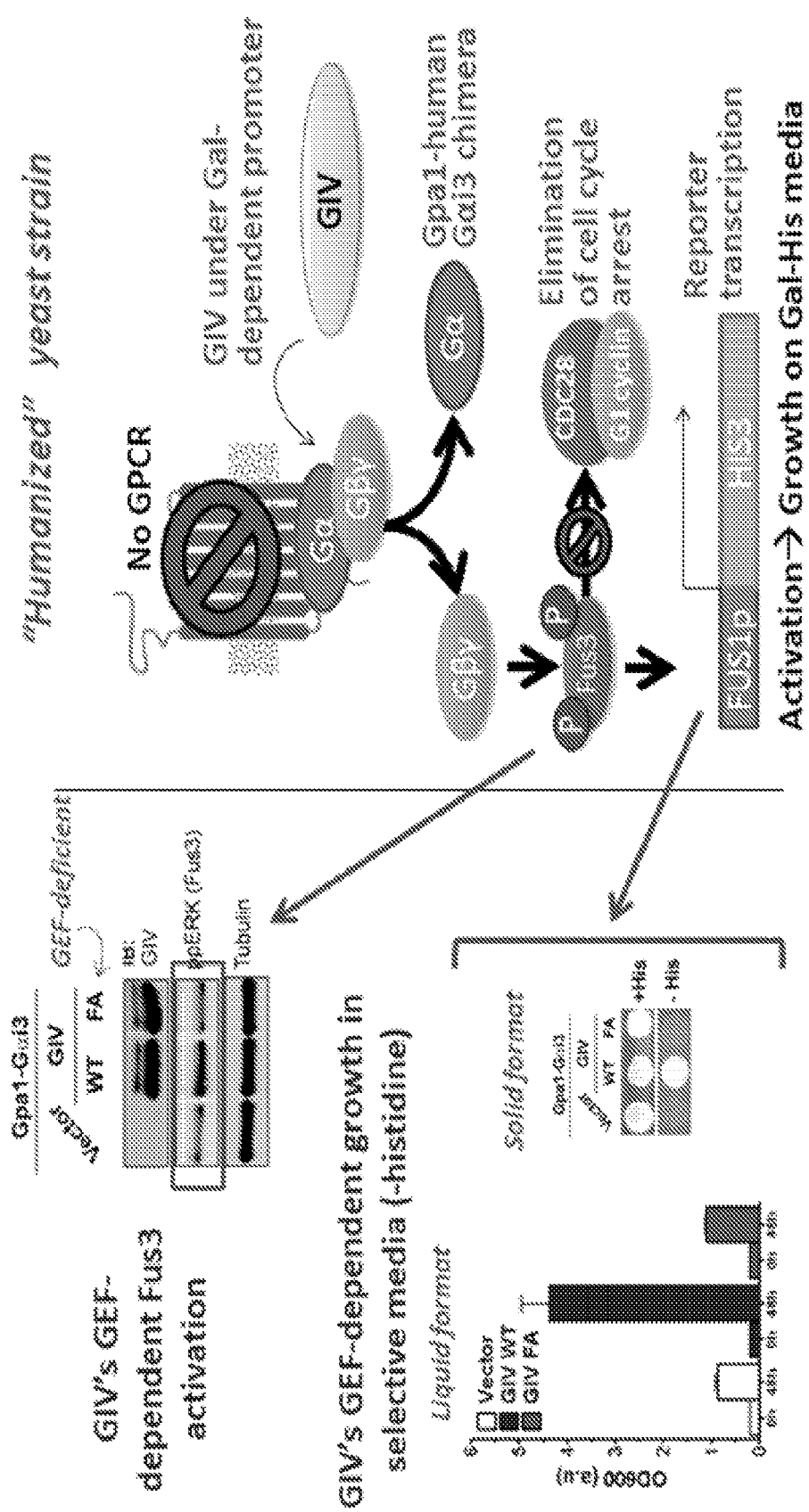
FIG. 13C. Follow-up assays (3) validation of a "humanized" yeast-based system to monitor G protein activation by GIV.

The present invention provides high-throughput screening assays to identify small molecule specific inhibitors of the GNAI:GIV interface as drug candidates, compositions and methods of use resulting therefrom. The screening assays of the present invention provide non-naturally occurring specific in vitro applications of inventive concepts in the form of unique research tools to identify drug candidates for further in vivo testing and therapeutic use.

It is to be understood that the invention is not limited in its application to the details of construction and the arrangement of components set forth in the following description or illustrated in the drawings.

When introducing elements of the present invention or the preferred embodiment(s) thereof, the articles "a", "an", "the" and "said" are intended to mean that there are one or more of the elements. The terms "comprising", "including"

and "having" are intended to be inclusive and mean that there may be additional elements other than the listed elements.

As used herein, "inhibit" or "inhibition" or "inhibits" refers to a reduction in normal activity, in embodiments a reduction below average minus 3 standard deviations, or minus 5 standard deviations.

As used herein, the term "pharmaceutical composition" contemplates compositions comprising one or more therapeutic compounds, agents or drugs as described below, and one or more pharmaceutically acceptable excipients, carriers, or vehicles.

As used herein, the term "pharmaceutically acceptable excipients, carriers, or vehicles" comprises any acceptable materials, and/or any one or more additives known in the art. As used herein, the term "excipients," "carriers," or "vehicle" refer to materials suitable for drug administration through various conventional administration routes known in the art. Excipients, carriers, and vehicles useful herein include any such materials known in the art, which are nontoxic and do not interact with other components of the composition in a deleterious manner, and generally refers to an excipient, diluent, preservative, solubilizer, emulsifier, adjuvant, and/or vehicle with which an active agent or drug is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art.

The present invention provides a research tool assay for identifying a specific modulator of GNAI, comprising: (a) combining a drug candidate with GNAI and a C-terminal GIV peptide and determining if the drug candidate inhibits GNAI interaction with the C-terminal GIV peptide; and (b) combining the drug candidate with GNAI and a DAPLE peptide and determining if the drug candidate inhibits GNAI interaction with DAPLE peptide. In embodiments, the drug candidate is identified as a specific modulator of GNAI when the drug candidate inhibits interaction with the C-terminal GIV peptide, and does not inhibit GNAI interaction with the DAPLE peptide.

In embodiments, the C-terminal GIV peptide comprises the amino acid sequence of SEQ ID NO: 1. In embodiments, the DAPLE peptide comprises the amino acid sequence of SEQ ID NO:2.

In embodiments, the determining steps are detected by fluorescent polarization.

The invention further provides a method of specifically modulating GNAI to treat a patient in need thereof, comprising administering to the patient an effective amount of a compound that inhibits GNAI interaction with a C-terminal GIV peptide, and does not inhibit GNAI interaction with DAPLE. In embodiments, the compound is ATA, or a functional analog or derivative thereof. In embodiments, the compound is NF023, or a functional analog or derivative thereof. In embodiments, the method is effective to treat cancer, fibrogenesis, diabetes, aging, or infertility.

The invention further provides a pharmaceutical composition comprising a pharmaceutically acceptable excipient and an effective amount of a compound that inhibits GNAI interaction with a C-terminal GIV peptide, and does not inhibit GNAI interaction with DAPLE. In embodiments, the compound is ATA, or a functional analog or derivative thereof. In embodiments, the compound is NF023, or a functional analog or derivative thereof. In embodiments, the method is effective to treat cancer, fibrogenesis, diabetes, aging, or infertility.

In embodiments, the invention provides an assay and method for screening for drug candidates which act as specific inhibitors against the GNAI:GIV interface. In embodiments, the invention provides an assay and method for screening a drug candidate using GIV or a fragment thereof comprising or consisting essentially of a small part of the GIV molecule (at least 31 aa on its C-terminus) (such as GIV peptide: KTGSPGSEVVTLQQFLEESNKLT-SVQIKSSS (SEQ ID NO: 1)). The identified GIV GBA peptide gives information on the GNAI:GIV interface and can be disrupted with small molecule drug candidates.

In a subsequent step, drug candidates that inhibit the GNAI:GIV interface are tested in a secondary screen involving GNAI:DAPLE, which will eliminate small molecules that do not have specificity against GNAI:GIV interface. Therefore, in this step, the drug candidate is screened for its inability to inhibit the GNAI:DAPLE interface using DAPLE or a fragment thereof comprising or consisting essentially of a small part of the molecule (such as DAPLE peptide: SASPSSEMVTLEEFLEESNRSSPTHDTP-SCRDDL (SEQ ID NO:2)). This will ensure identifying specific inhibitors that will not cross-inhibit the GNAI:DAPLE interface (with which GNAI:GIV interface shares similarities), because DAPLE's ability to bind and activate GNAI is critical for tumor suppression and inhibiting that interface (as a potential side effect of inhibitors against the GNAI:GIV interface) is highly undesirable.

As for the first step in the assay, this small region of 31 aa GIV peptide: KTGSPGSEVVTLQQFLEESNKLT-SVQIKSSS (SEQ ID NO: 1) was arrived at after careful biochemistry determined that anything less than this is less efficient in binding or activation the G protein, GNAI. The invention provides that this peptide sequence can be adapted in HTP screens to accurately pick up the effective agonists/antagonists against the druggable interface GNAI:GIV.

As for the second step, it is not common knowledge that the orthologue of GIV, DAPLE, also binds GNAI and uses a similar hydrophobic binding cleft on which GIV docks. It was discovered that DAPLE's ability to bind GNAI has differences from how GIV binds GNAI. It is these differences that achieve specificity of molecular inhibitors to target the GNAI:GIV interface, without affecting the GNAI:DAPLE interface. The DAPLE peptide SASPS-SEMVTLEEFLEESNRSSPTHDTPSCRDDL (SEQ ID NO:2) is the appropriate secondary screen to eliminate the molecules that non-specifically target both GNAI:GIV and GNAI:DAPLE interfaces.

As will be appreciated, performing the first step described above initially will insure the second step is screening for effective inhibitors, however, the invention contemplates that the order of the steps can be reversed. The invention contemplates compositions comprising the tools and reagents necessary for conducting the screening assays, in particular screening for molecules which selectively inhibit the GNAI interface with molecules comprising, or consisting essentially of, the GIV peptide KTGSPGSEVVTLQQFLEESNKLTSVQIKSSS (SEQ ID NO: 1) or the DAPLE peptide SASPSSEMVTLEEFLEESNRSSPTHDTPSCRDDL (SEQ ID NO:2), and a detectable moiety.

EXAMPLES

Example 1

A pilot screen of the LOPAC1280 library (collection of known bioactive compounds) was conducted and identified lead compounds with inhibitory activity (FIG. 11A). A virtual ligand screen (VLS) of the same library (LOPAC1280) was conducted using in silico docking methods [33-35] (FIG. 11B). The results from both screens were compared. From the FP assay only three "hits" (FIG. 11C) were identified, i.e, a ~0.25%, hit rate, indicating that the assay is not non-specifically affected by too many compounds. From the virtual screen 7 'hits' (FIG. 11B) were identified. Importantly, 2 of the virtual screen hits matched the results from the FP assay and a third was validated as a GIV:Gαi inhibitor. Compounds were validated by dose response curves (FIG. 11D). ATA and NF023 (identified by both screens) displayed $IC_{50}$'s of ~5 μM while suramin (found only in virtual screen) had lower potency ($IC_{50}$~805 μM), consistent with why it was not detected by the FP screen (FIG. 11A). None of the other 4 hits predicted by the VLS inhibited binding. Using a GST-pulldown assay, it was confirmed that ATA and NF023 are true hits while topotecan was as a false positive (FIG. 11E). Interestingly, the virtual screen correctly predicts topotecan as an ineffective/non-binding compound (FIG. 11B).

The invention provides therapeutic compositions comprising compounds identified by the screening methods, and analogs and derivatives thereof, in a pharmaceutically acceptable excipient. Exemplary compounds provided by the screening assay of the present invention are aurintricarboxylic acid (ATA) and 8,8'-[carbonylbis(imino-3,1-phenylenecarbonylimino)]bis(1,3,5-naphthalene-trisulfonic acid) hexasodium salt (NF-023) and 4-[3-(4-Acetyl-3-hydroxy-2-propylphenoxy)propxylphenoxyacetic acid (L-165, 041). ATA is listed as a DNA topoisomerase II inhibitor in the Sigma LOPAC library database, and it has also been shown to inhibit cysteine proteases such as calpain and caspases 3, 6, 7, and 9. NF-023 is listed as a potent, selective P2X1 receptor antagonist in the Sigma LOPAC library database, and is an analog of suramin, a hexasulfonated naphthylurea.

A.

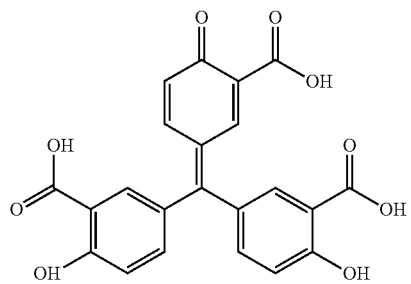

Aurintricarboxylic acid (ATA)

B.

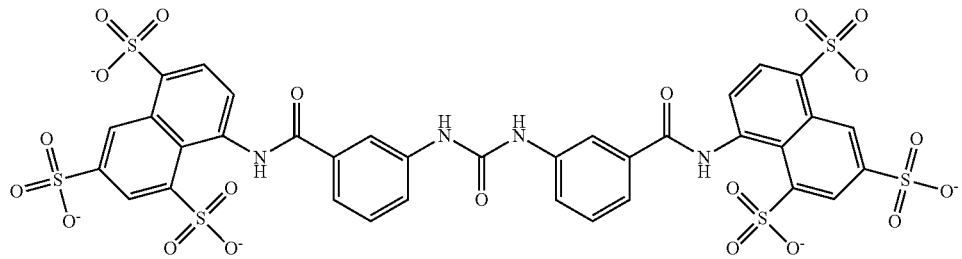

8,8'-[carbonylbis(imino-3,1-phenylenecarbonylimino)]bis(1,3,5-naphthalene-trisulfonic acid hexassodium salt (NF-023)

C.

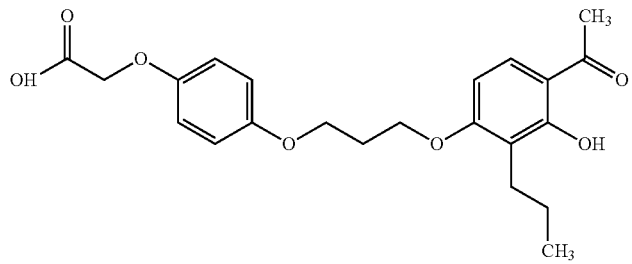

4-[3-(4-Acetyl-3-hydroxy-2-propylphenoxy)propxy]phenoxyacetic acid (L-165.041)

DISCUSSION

GIV can be referred to as a GEM because of its ability to serve as a GEF [activator] of GNAI as well as a GDI [inhibitor] for GNAS. By working in this sort of dual mode, GIV-GEM can coordinately lower cellular cAMP levels by activating the inhibitor of adenylyl cyclase [GNAT] and inhibiting the stimulator of adenylyl cyclase [GNAS]. This is unlike what happens in the case of GPCRs, the most drugged/targeted component of cAMP signaling to date. (see FIG. 15). Key differences also include the fact that while GPCRs can only either activate only trimeric forms of Gi or Gs at a time, and such signaling is finite and only initiated at the PM by ligand-bound receptors, GEMs like GIV can activate monomeric GNAI or inhibit monomeric GNAS by either capturing them during the cyclical activation-inactivation process or by generating monomers of alpha subunit from trimers or GDI bound complexes [in the case of GNAT]. Last, but not least, signaling via GEM like GIV is prolonged, and can occur on internal membranes. This makes GEMs more versatile, and signaling via them more robust.

Figure 15:
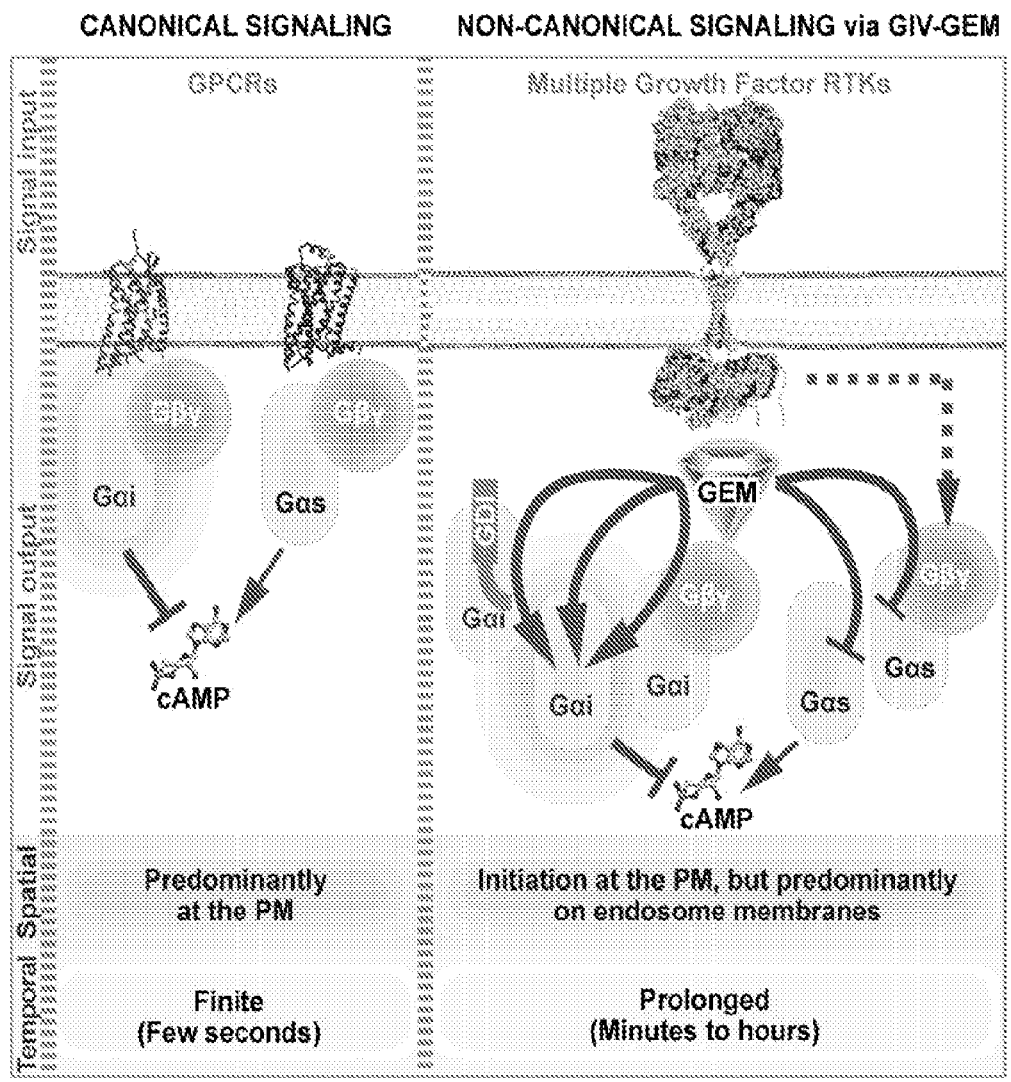
FIG. 15. Schematic shows how canonical signaling from GPCR to cAMP at the plasma membrane (PM) lasts for a finite time period whereas non-canonical cAMP, activity through RTK-GIV-GEM interactions and compartmentalization of Gαi and Gαs at the PM and endosome respectively, can lead to prolonged signals.

FIG. 15 shows schematic [modified from Ghosh P et al., Cell Cycle, 2017] shows how canonical signaling from GPCR to cAMP at the plasma membrane (PM) lasts for a finite time period whereas non-canonical cAMP activity, through RTK-GIV-GEM interactions and compartmentalization of Gαi and Gαs at the PM and endosome respectively, can lead to prolonged signals.

Figure 16:
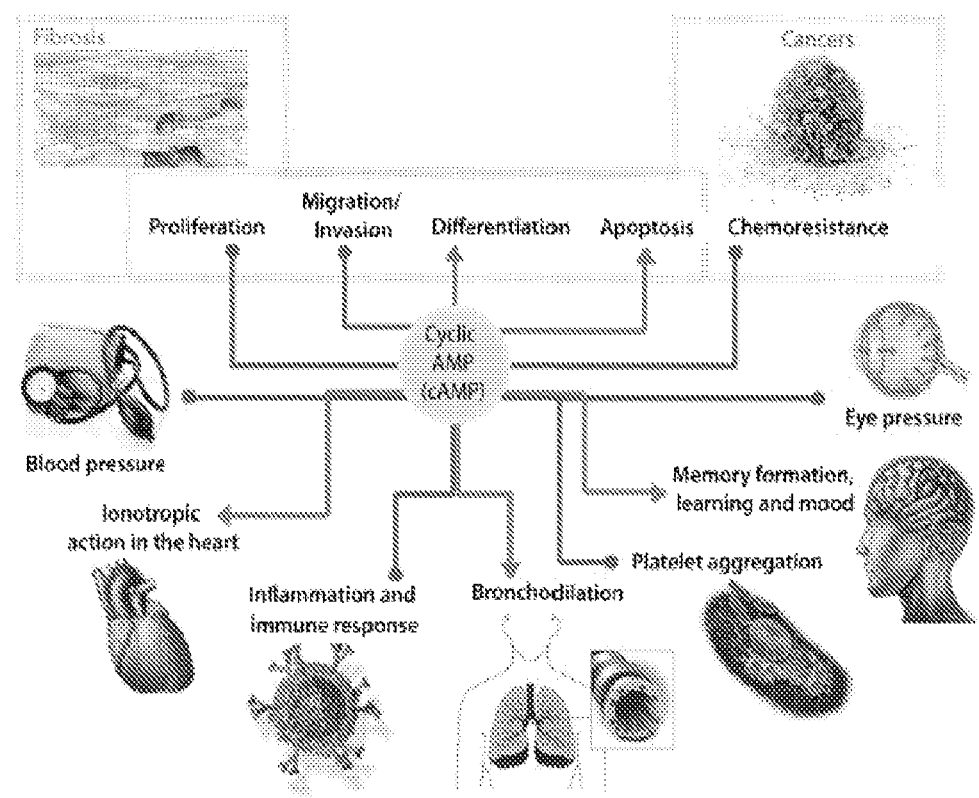
FIG. 16. Schematics summarizing the role of cyclic AMP (cAMP) in diverse biological processes.

The reason GIV-GEM and other GEMs can be major targetable components is because cAMP is most important in the biological activities shown in FIG. 16. cAMP plays an important role in regulating many physiological conditions ranging from blood pressure to memory formation. Particularly, in the context of cancers (top right), cAMP is largely protective as it inhibits proliferation, invasion, chemoresistance, and promotes apoptosis and differentiation of tumor cells. Similarly, in the context of organ fibrosis, cAMP is a potent anti-fibrotic agent because it inhibits proliferation and migration and triggers apoptosis and return to quiescence for myofibroblasts, the major cell type implicated in fibrogenic disorders. It is noteworthy that although cAMP modulatory drugs, either targeting GPCRs or phosphodiesterases [PDEs] are available for most of the diseases noted in the bottom of FIG. 16, no such therapy has reached fruition in the case of organ fibrosis and cancers.

The Gbetagamma dependent component of signaling that is initiated when GIV-GEMs release free Gbg subunits from GNAI and GNAS, has been shown to be important for signaling via PI3K, Rac1 and other such intermediates. Therefore, GIV-GEM initiates two pronged signaling: cAMP via GNAI/GNAS [alpha subunits of heterotrimeric G proteins] and Gbetagamma signaling via its own intermediates. Both components are important for the holistic impact of GIV-GEM in disease states.

Recent work using systems biology has shown that levels of GIV-GEM being high vs low acts like a tunable valve for cAMP flow in signaling circuits. Briefly, systems approach was used to build a circuit for growth factor dependent cAMP signaling via G proteins, GNAI and GNAS. The model was first validated using cell based and biochemical assays for key reaction steps. The model captured the key observed dynamics of EGFR-GIV-G protein complex formation, GNAS-GIV complex formation, and then cAMP, PKA and pCREB signaling. This model inquires as to what impact does high vs low GIV have on cAMP signaling downstream of growth factors. Results of such simulations are shown in FIG. 17.

Non-canonical growth factor-dependent cAMP signaling is prolonged and largely on internal membranes.

Figure 17:
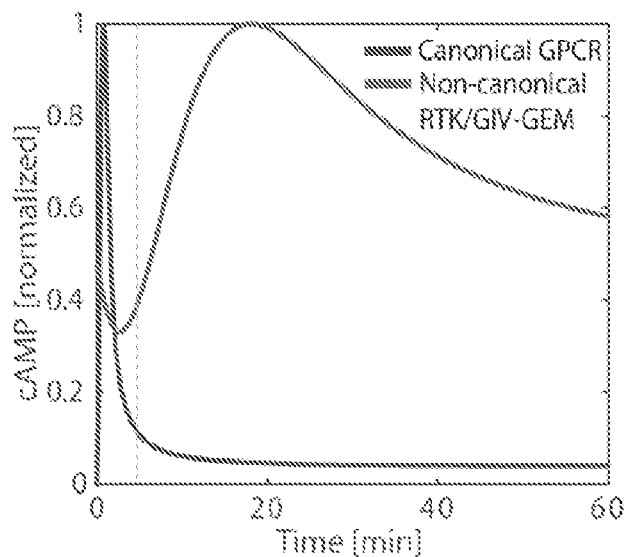
FIG. 17. Non-canonical growth factor-dependent cAMP signaling is prolonged and largely on internal membranes.

FIG. 17 shows non-canonical RTK mediated cAMP dynamics through GIV-GEM has prolonged time scales due to both PM and endosomal signaling as compared to canonical GPCR mediated cAMP activation at the PM alone. The interrupted line at ~5 min indicates the time period when ligand activated EGFR is typically rapidly endocytosed, marking a watershed between end of PM and beginning of endosomal phase of signaling.

Using systems approaches determined that GIV-GEM operates in 2 regimes. See figures and legend below. The GEF effect on GNAI is a predominant effect early on. The GDI effect on GNAS is the predominant effect later.

Figure 18:
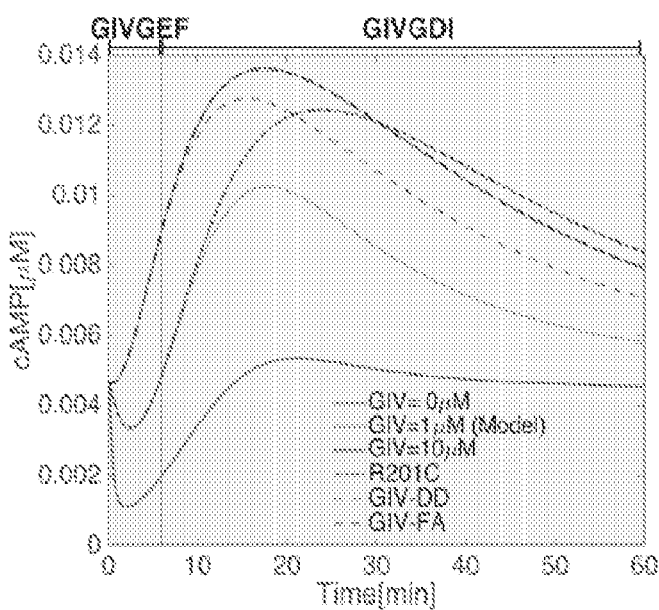
FIG. 18. Simulations identify the two distinct regimes of GIV GEM's effect on cAMP dynamics.

FIG. 18 shows that simulations identify the two distinct regimes of GIV GEM's effect on cAMP dynamics. The early 0-5 min phase is characterized by a dip in cAMP concentration; GIV's GEF function on Gαi dominates in this phase. This is followed by a delayed ~10-60 min phase which is characterized by an increase in the concentration of cAMP; GIV's GDI function on Gas dominates this phase. Simulations predict that cAMP dynamics will decrease with increasing GIV expression. Compare the control GIV in the model with the high GIV and the low GIV lines. In high GIV states, the transition from GIV-GEF dominant (early, ~0-5 min) to GIV-GDI dominant (late, ~10-60 min) regimes is evident as the line transitions from negative to positive. Simulations for cAMP dynamics are also displayed for 3 other conditions: 1) GIV in the absence of its GEF effect on Gαi (the GIV-DD mutant), in the absence of its GDI effect (as would be mimicked by a constitutively active Gas R201C mutant), and in the absence of both its GEF and GDI effects (GIV-FA mutant). GIV-DD doesn't show the initial decrease in cAMP concentration (dashed line), while loss of GIV's GDI function results in an initial decrease in cAMP concentration but also a prolonged increase in cAMP (dot dashed line). The effect of GIV-FA (dashed lines) on cAMP concentration is the same as that of low GIV (line).

Figure 19:
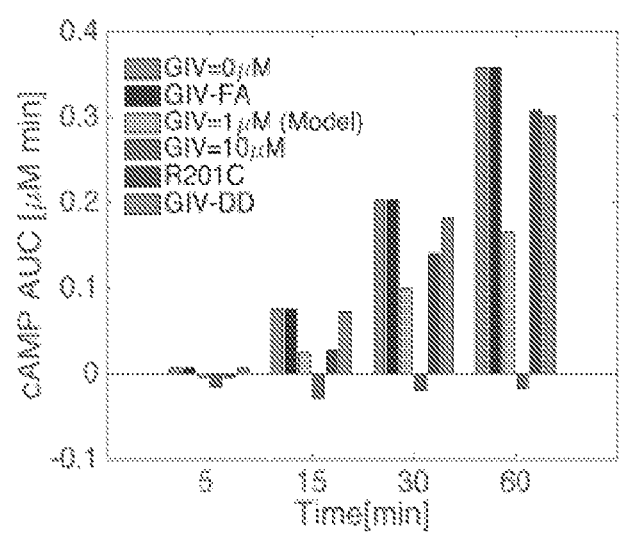
FIG. 19. The area under the curve (AUC) for cAMP dynamics was calculated for different time points after EGF stimulation.

FIG. 19 shows the area under the curve (AUC) for cAMP dynamics was calculated for different time points after EGF stimulation. The transition from GIV-GEF dominant (early, ~0-5 min) to GIV-GDI dominant (late, ~10-60 min) regimes is evident in the transition from AUC going from negative to positive [in high GIV states]. The AUC remains negative at all times for GIV=10 μM, indicating that cAMP levels do not increase when GIV is high.

Figures 20A, 20B, 20C:
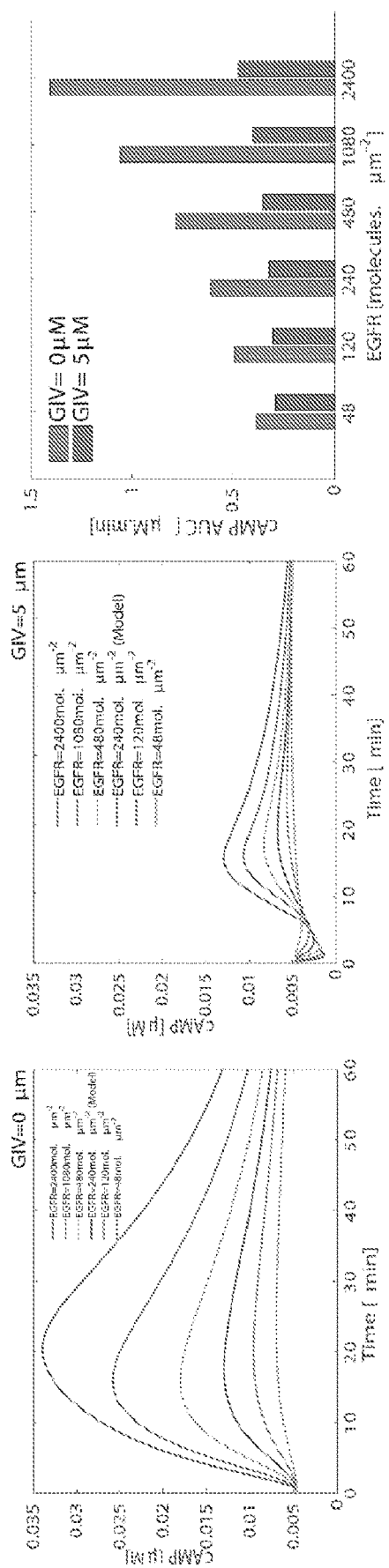
FIGS. 20A-20C.

FIGS. 20A-20C demonstrate a systems approach showing that low GIV states are very sensitive, i.e., increasing growth factors elicits higher cAMP responses. However, when GIV levels are high, increasing stimuli does not elicit higher cAMP response. When the concentration of GIV is zero, simulations predict that increasing EGFR copy number results in increasing cAMP (FIG. 20A) When GIV concentration is high (5 μM), simulations predict that cAMP concentration does not vary much in response to increasing EGFR copy number (FIG. 20B) The increase in cAMP AUC over time is pronounced for GIV=0 μM (green bars) while there is a very small change in the AUC over time for GIV=5 μM (FIG. 20C).

Figure 21A:
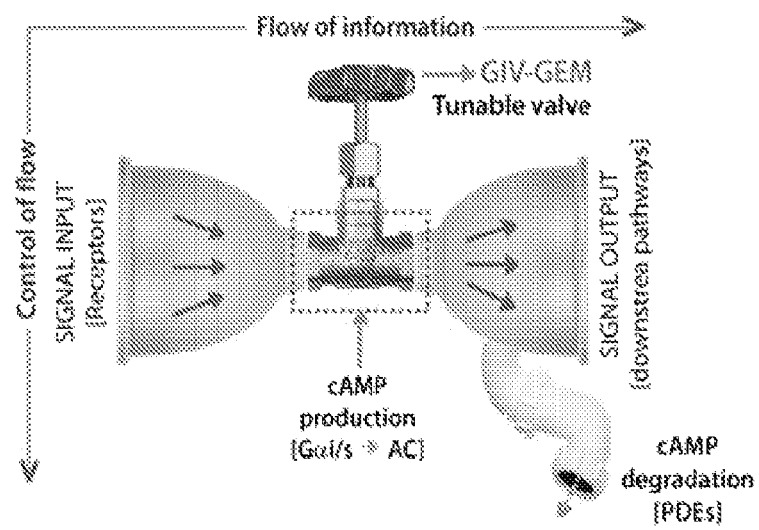
FIGS. 21A-21B. Schematic displays the workings of GIV-GEM within cellular signaling circuit.
Figure 21B:
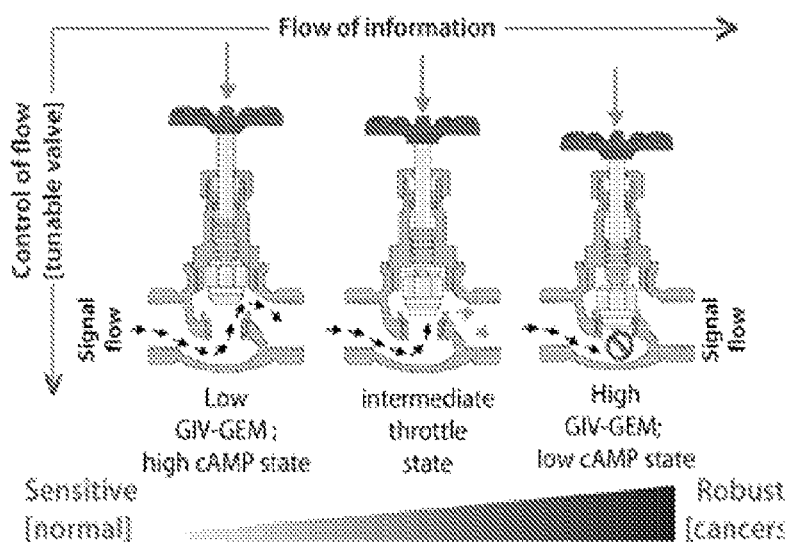

Based on the above, it can be concluded that GIV-GEM serves as a tunable valve for cAMP signaling:

FIGS. 21A-21B provide schematic displays of the workings of GIV-GEM within cellular signaling circuit. FIG. 21A shows a variety of environmental stimuli [input signals; left] are integrated into core proteins [center] that activate downstream target proteins such as transcription factors [output signals; right]. The flow of information [left to right] is believed to conform to a bow tie structure. Cellular concentrations of cAMP is a key determinant of robustness at the core of information flow [Friedlander and Alon; PLoS Computational Biology; 2015; journals.plos.org/ploscompbiol/article?id=10.1371/journal.pcbi.1004055]; levels are antagonistically balanced by Gαi/Gαs and AC production and degradation by PDEs [sink pipe]. GIV-GEM serves as a tunable valve, allowing cells to fine-tune the concentrations of cAMP in cells as shown in FIG. 21B shows altered expression and/or function of GIV-GEM allows tunability of cAMP signals such that when GEM expression/activity is lowest, increasing input signals can trigger some of the highest levels of cellular cAMP, thereby conferring sensitivity. When GEM expression/activity is highest, cAMP levels are lowest, regardless of the amount of input signals, thereby conferring robustness.

Therefore, the invention provides strategies for drug development in GIV-driven diseases.

The best drugs to target this novel modulator of cAMP and elevate cAMP levels in disorders characterized by HIGH-GIV and low-cAMP [like invasive cancers and fibrogenic diseases] is to tackle both GEF and GDI functions of GIV. The Gbetagamma side of signaling will be automatically stopped if GIV can be inhibited from activating trimeric G proteins Gi or inhibiting trimeric Gs.

So as to not block any G protein signaling via canonical pathways, avoid targeting the G protein, or finding molecules that can sit in transient pockets created during nucleotide exchange. Finding such molecules may be acceptable for some biochemical research use, but will derail canonical G protein signaling cascades via GPCRs.

The addition of PDE inhibitors to GIV-inhibitors should provide adjuvant benefit PDE inhibitors will reduce cAMP removal, and further augment cAMP conc in cells.

The preferred molecules will be those that can bind GIV and alter the exposure of the GEM module on GIV which has a dual role and can serve as GEF and GDI on two G proteins. This should be possible because it has been published earlier [Lin C et al., MBoC 2014] that GIV's CT is intrinsically disordered, and when bound to proteins, it is known to change conformation.

The preferred molecules will also be those which can bind GIV and target it for degradation, effectively reducing the copy numbers in cells. This is a possibility because the protein may be rendered as 'poorly folded or wrongly folded' when bound to 'drug,' and such forms may be targeted by cells for degradation. Thus, a part of small molecule drug candidate screening, levels of GIV mRNA and protein can be measured in cells, such as by qPCR and Immunoblotting; while proteins should be reduced, in proteasome-dependent manner, mRNA could remain detectable/constant/go down due to the loss of positive feedback loop between STAT3 [transcriptional activator of GIV] and GIV [which activates STAT3 signaling via GEM function] (Dunkel Y et al., JBC 2011).

In embodiments, the invention provides a screen for small molecules that disrupt GIV-CT's [~210 aa] ability to bind or modulate nucleotide exchange in Gαi or Gαs. This screening research tool assay can comprise the following steps.

Step 1—Protein-protein interaction assay: any kind [by any assay, FP, or others]

i. pre-incubate GIV-CT with small molecules. One may pre-screen at this stage to find which molecules are binding to GIV using either CD spectroscopy or other methods;

ii. add G proteins, either Gαi and Gαs to the reaction; and iii. identify some negative or some positive allosteric modulators of GEM function (NAMs and some PAMs).

In Step 2—Measure enzyme activity [by GTPase assays-HTP methods].

If STEP 2 is carried out before STEP 1, then do pre-incubation with small molecules, then remove excess of the unbound molecules, before exposing the G proteins to exchanging conditions. This will avoid the possible jamming of some of the molecules in pockets of G proteins exposed during transition states of exchange.

If the above caution cannot be done, then extra step should be included that G proteins Gαi and Gαs with small molecule alone should be incubated and tested for their ability to inhibit or alter in any way the basal nucleotide exchange observed in monomeric alpha subunits in vitro.

In Step 3—Cell-based assays:

i. GIV protein levels by immunoblotting, ii. GIV mRNA by qPCR, iii. cAMP assays—kits commercial, iv. pAkt, other signaling pathways, AND v. cell invasion, apoptosis, proliferation, differentiation, stemness.

These and other features of the embodiments of the invention will become apparent to the skilled artisan upon a review of the present disclosure and appended claims.

What is claimed is:

1. A research tool assay for identifying a specific modulator of guanine nucleotide-binding protein alpha (GNAI), comprising
   a. combining a drug candidate with GNAI and a C-terminal Girdin (GIV) peptide comprising the amino acid sequence of SEQ ID NO:1 and determining if the drug candidate inhibits GNAI interaction with the C-terminal GIV peptide; and
   b. combining the drug candidate with GNAI and a Dvl-associated protein with high frequency of leucine (DAPLE) peptide comprising the amino acid sequence of SEQ ID NO:2 and determining if the drug candidate inhibits GNAI interaction with the DAPLE peptide,
   wherein the drug candidate is identified as a specific modulator of GNAI when the drug candidate inhibits interaction with the C-terminal GIV peptide, and does not inhibit GNAI interaction with the DAPLE peptide.

2. The assay of claim 1, wherein the determining steps are detected by fluorescent polarization.

* * * * *

SEQUENCE LISTING

<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

Lys Thr Gly Ser Pro Gly Ser Glu Val Val Thr Leu Gln Gln Phe Leu
1               5                   10                  15

Glu Glu Ser Asn Lys Leu Thr Ser Val Gln Ile Lys Ser Ser Ser
            20                  25                  30

<210> SEQ ID NO 2
<211> LENGTH: 34
<212> TYPE: PRT
<213> ORGANISM: Homo sapiens

<400> SEQUENCE: 2

Ser Ala Ser Pro Ser Ser Glu Met Val Thr Leu Glu Glu Phe Leu Glu
1               5                   10                  15

Glu Ser Asn Arg Ser Ser Pro Thr His Asp Thr Pro Ser Cys Arg Asp
            20                  25                  30

Asp Leu